(12) United States Patent
Green et al.

(10) Patent No.: US 10,438,783 B2
(45) Date of Patent: Oct. 8, 2019

(54) THEORETICAL COLLISION CROSS SECTION ("CCS") IN EXPERIMENTAL DESIGN

(71) Applicant: Micromass UK Limited, Wilmslow (GB)

(72) Inventors: Martin Raymond Green, Bowdon (GB); Kevin Giles, Stockport (GB); Keith Richardson, Derbyshire (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 378 days.

(21) Appl. No.: 15/125,406

(22) PCT Filed: Mar. 10, 2015

(86) PCT No.: PCT/GB2015/050703
§ 371 (c)(1),
(2) Date: Sep. 12, 2016

(87) PCT Pub. No.: WO2015/136274
PCT Pub. Date: Sep. 17, 2015

(65) Prior Publication Data
US 2017/0254776 A1    Sep. 7, 2017

(30) Foreign Application Priority Data

Mar. 10, 2014 (EP) .................................... 14158643
Mar. 10, 2014 (GB) .................................. 1404195.8

(51) Int. Cl.
*H01J 49/00* (2006.01)
*G01N 27/62* (2006.01)

(52) U.S. Cl.
CPC ........ *H01J 49/0036* (2013.01); *G01N 27/622* (2013.01); *H01J 49/004* (2013.01); *H01J 49/005* (2013.01); *H01J 49/0031* (2013.01)

(58) Field of Classification Search
CPC .. H01J 49/0036; H01J 49/0031; H01J 49/005; H01J 49/004; G01N 27/622
See application file for complete search history.

(56) References Cited

U.S. PATENT DOCUMENTS

| 6,495,824 B1 | 12/2002 | Atkinson |
| 6,831,273 B2 | 12/2004 | Jenkins et al. |
| 7,812,305 B2 | 10/2010 | Miller et al. |
| 8,242,442 B2 | 8/2012 | Krueger et al. |
| 8,278,620 B2 | 10/2012 | Schwartz et al. |

(Continued)

FOREIGN PATENT DOCUMENTS

| GB | 2393849 A | 4/2004 |
| GB | 2490792 A | 11/2012 |

(Continued)

OTHER PUBLICATIONS

Bush et al., "Collision Cross Sections of Proteins and Their Complexes: a Calibration Framework and Database for Gas-Phase Structural Biology" Analytical Chemistry, vol. 82, No. 22, p. 9557-9565, Nov. 2010.

(Continued)

*Primary Examiner* — Samuel P Siefke

(57) ABSTRACT

A method of mass spectrometry is disclosed comprising calculating an ion mobility value, collision cross section or interaction cross section of a plurality of different analyte ions under one or more different analytical conditions, and setting one or more operational parameters of a mass spectrometer in response to the calculated ion mobility values, collision cross sections or the calculated interaction cross sections so as to maximize or enhance a subsequent ion mobility separation of a plurality of different analyte ions.

19 Claims, 1 Drawing Sheet

(56) References Cited

U.S. PATENT DOCUMENTS

| | | |
|---|---|---|
| 8,384,024 B2 | 2/2013 | Miller et al. |
| 8,525,106 B2 | 9/2013 | Muntean |
| 8,618,477 B2 | 12/2013 | Krueger et al. |
| 8,921,778 B2 | 12/2014 | Atkinson et al. |
| 2005/0048564 A1 | 3/2005 | Emili et al. |
| 2006/0234326 A1 | 10/2006 | Cerda |
| 2007/0114382 A1 | 5/2007 | Clemmer et al. |
| 2010/0108877 A1 | 5/2010 | Wu et al. |
| 2010/0127166 A1 | 5/2010 | Krueger et al. |
| 2010/0224770 A1 | 9/2010 | Burns et al. |
| 2011/0266426 A1 | 11/2011 | Schwartz et al. |
| 2012/0171679 A1 | 7/2012 | Ecker et al. |
| 2013/0009053 A1 | 1/2013 | Wu |
| 2013/0218478 A1 | 8/2013 | Campuzano et al. |
| 2016/0054264 A1 | 2/2016 | Carver et al. |

FOREIGN PATENT DOCUMENTS

| | | |
|---|---|---|
| WO | 2004/012231 | 2/2004 |
| WO | 2006/114580 A1 | 11/2006 |

OTHER PUBLICATIONS

Fernandez-Maestre et al., "Buffer Gas Modifiers Effect Resolution in Ion Mobility Spectrometry Through Selective Ion-Molecule Clustering Reactions", Rapid Communications in Mass Spectrometry, vol. 26, No. 19, p. 2217-2222, Sep. 2012.

Fernandez-Maestre et al., "Using a Buffer Gas Modifier to Change Separation Selectivity in Ion Mobility Spectrometry", Journal of Mass Spectrometry, vol. 298, No. 1-3, p. 2-9, Dec. 2010.

Green et al., "Modification of Ion Mobility Separation Using Volatile Organic Dopants on a Quadrupole-Ion Mobility-Orthogonal Time-Of-Flight Mass Spectrometer", Proceedings $59^{th}$ ASMS, 2011.

Knapman et al., "Considerations in Experimental and Theoretical Collision Cross-Section Measurements of Small Molecules Using Travelling Wave Ion Mobility Spectrometry-Mass Spectrometry", International Journal of Mass Spectrometry, Elsevier Science Publishers, vol. 298, No. 1-3, p. 17-23, Dec. 2010.

Lapthorn et al., "Ion Mobility Spectrometry-Mass Spectrometry (IMS-MS) of Small Molecules: Separating and Assigning Structures to Ions", Mass Spectrometry Reviews, vol. 31, No. 1, p. 43-71, Aug. 2012.

Shvartsburg et al., "An Exact Hard-Spheres Scattering Model for the Mobilities of Polyatomic Ions", Chemical Physics Letters, p. 86-91, Oct. 1996.

Dwivedi et al., "Rapid Resolution of Carbohydrate Isomers by Electrospray Ionization Ambient Pressure Ion Mobility Spectrometry-Time-of-Flight Mass Spectrometry (ESI-APIMS-TOFMS)", Focus: From Mobilities to Proteomes, p. 1163-1175, Apr. 2007.

Williams et al., "Use of Ion Mobility Mass Spectrometry and a Collision Cross-Section Algorithm to Study an Organometallic Ruthenium Anticancer Complex and its Adducts with a DNA Oligonucleotide", RCM, p. 3563-3569, Jun. 2009.

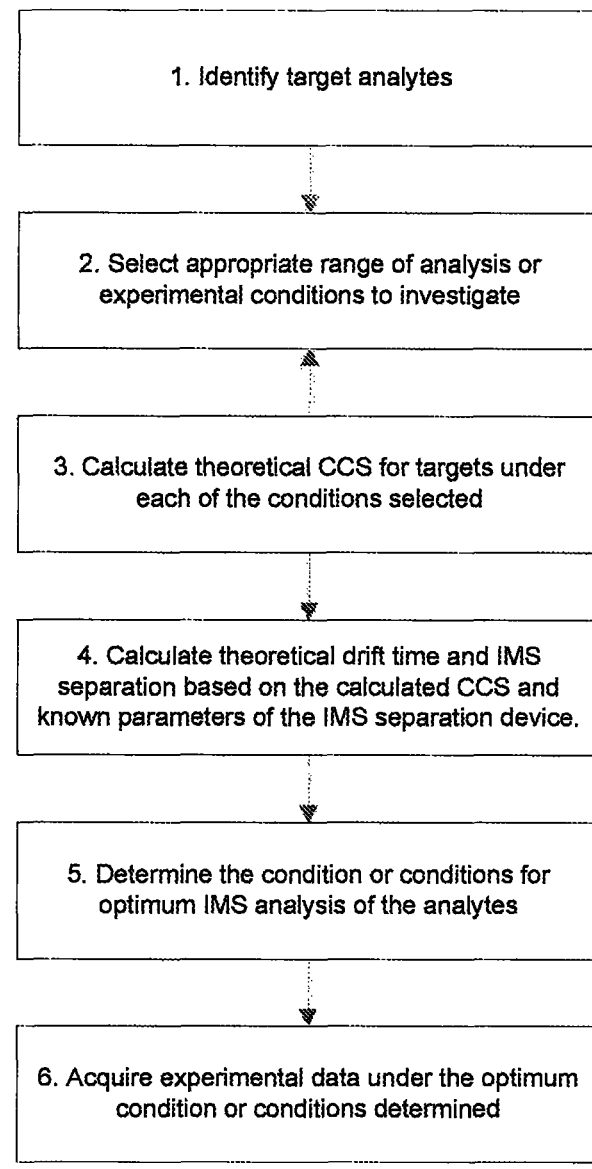

THEORETICAL COLLISION CROSS SECTION ("CCS") IN EXPERIMENTAL DESIGN

CROSS REFERENCE TO RELATED APPLICATIONS

This application is the National Stage of International Application No. PCT/GB2015/050703, filed 10 Mar. 2015 which claims priority from and the benefit of United Kingdom patent application No. 1404195.8 filed on 10 Mar. 2014 and European patent application No. 14158643.8 filed on 10 Mar. 2014. The entire contents of these applications are incorporated herein by reference.

FIELD OF THE INVENTION

The present invention relates generally to the field of mass spectrometry and in particular to methods of mass spectrometry and mass spectrometers.

BACKGROUND

Ion mobility spectrometry or separation ("IMS") represents a powerful method of separating and identifying ions, especially when coupled with liquid chromatography ("LC") and mass spectrometry ("MS") techniques. However, there are many instances where the IMS resolution is not sufficient to separate ions that have very similar Collision Cross Sections ("CCS") or interaction cross sections.

The Collision Cross Section ("CCS") or interaction cross section measured for a particular analyte depends on the nature of the ions produced from the analyte during or after the ionization process, and also on the conditions within the measurement device, such as the composition of the drift gas within an ion mobility spectrometry or separation device.

It is known to attempt to optimise the separation of ions in an ion mobility spectrometry or separation device for specific analytes. The optimal ion mobility conditions for a given analyte are determined by experimentally analysing the same analyte under each of several different conditions. However, this optimization is done empirically and involves a great deal of time consuming experimentation. Furthermore, this approach of non-directed experimentation may not ultimately lead to a satisfactory result.

Reference is made to Prabha Dwivedi, Brad Bendiak, Brian H. Glowers, Herbert H. Hill Jr. "Rapid Resolution of Carbohydrate Isomers by Electrospray Ionization Ambient Pressure Ion Mobility Spectrometry-Time-of-Flight Mass Spectrometry (ESI-APIMS-TOFMS)". In this paper controlling the charge carrier during positive ion ionization of carbohydrates allows isomeric pairs to be resolved by ion mobility.

Reference is also made to: Rapid Commun. Mass Spectrom. 2009; 23: 3563-3569 "Use of ion mobility mass spectrometry and a collision cross-section algorithm to study an organometallic ruthenium anticancer complex and its adducts with a DNA oligonucleotide." This paper illustrates an approach for calculation of theoretical cross section for known organometallic compounds.

It is desired to provide an improved method of mass spectrometry.

SUMMARY

According to an aspect there is provided a method of mass spectrometry comprising:

calculating an ion mobility value, collision cross section or interaction cross section of a plurality of different analyte ions under one or more different analytical conditions, and setting one or more operational parameters of a mass spectrometer in response to the calculated ion mobility values, collision cross sections or interaction cross sections so as to maximise or enhance a subsequent ion mobility separation of a plurality of different analyte ions.

An embodiment relates to a method of mass spectrometry in which a collision cross section or interaction cross section is theoretically calculated for each of a plurality of different analyte ions under one or more different analytical conditions. One or more operational parameters of a mass spectrometer are then may set based on the theoretically calculated collision cross sections or the calculated interaction cross sections so as to maximise or enhance a subsequent ion mobility separation of the plurality of different analyte ions.

According to an embodiment, theoretical calculations of the collision cross sections or interaction cross sections of a plurality of different analyte ions under one or more different analytical conditions may be used to determine an optimal set of analytical conditions and/or operation parameters under which the ion mobility separation of the plurality of different analyte ions will be maximised or enhanced. In this way, the ability of the mass spectrometer to properly separate and identify the analytes from which the plurality of different analyte ions are derived can may be correspondingly maximised or enhanced.

Using theoretical calculations of the collision cross sections or interaction cross sections in accordance with an embodiment advantageously reduces the time and effort required to find the optimal set of analytical conditions and/or operation parameters when compared with the known empirical experimental methods, and also conserves samples, which in many cases may be difficult to obtain in sufficient quantity for extensive experimental optimisation.

The embodiment described above represents a systematic approach for predicting the optimal experimental conditions for either ionization and/or ion mobility spectrometry or separation for specific analytes.

It will be appreciated therefore that an improved method of mass spectrometry is provided.

According to an embodiment, the step of calculating an ion mobility value, collision cross section or interaction cross section of a plurality of different analyte ions under one or more different analytical conditions comprises calculating an ion mobility value, collision cross section or interaction cross section of a plurality of different analyte ions under two or more different analytical conditions.

According to an embodiment, the plurality of different analyte ions relate to the same analyte but have different forms, structures, states or other properties.

According to an embodiment, the plurality of different analyte ions relate to different analytes having different compositions, forms, structures, states or other properties.

According to an embodiment, the method comprises:

determining, calculating or predicting a plurality of different analyte ions which may be generated from one or more analytes of interest under one or more of the different analytical conditions;

wherein the step of calculating the ion mobility value, collision cross section or interaction cross section of the plurality of different analyte ions under the one or more different analytical conditions comprises calculating an ion mobility value, collision cross section or interaction cross section for one or more of the determined, calculated or predicted different analyte ions.

According to an embodiment, the step of setting the one or more operational parameters of the mass spectrometer comprises:

selecting one or more of the one or more different analytical conditions based on the calculated ion mobility values, collision cross sections or interaction cross sections so as to maximise or enhance the subsequent ion mobility separation of the plurality of different analyte ions; and setting the one or more operational parameters of the mass spectrometer so as to produce the one or more selected analytical conditions.

According to an embodiment, the method comprises separating the plurality of different analyte ions according to their ion mobility one or more times using the mass spectrometer.

According to an embodiment, the method comprises separating the plurality of different analyte ions according to their rate of change of ion mobility with electric field strength one or more times using the mass spectrometer.

According to an embodiment, the method comprises generating the plurality of different analyte ions using the mass spectrometer.

According to an embodiment, the method comprises mass analysing the plurality of different analyte ions using the mass spectrometer.

According to an embodiment, the method comprises:

calculating one or more additional physico-chemical or other properties of the plurality of different analyte ions under the one or more different analytical conditions; and setting one or more operational parameters of the mass spectrometer based on the calculated additional physico-chemical or other properties so as to maximise or enhance the subsequent ion mobility separation of the plurality of different analyte ions.

According to an embodiment, the one or more additional physico-chemical or other properties comprise peak shape, peak width, peak skew, number of peaks, and/or peak kurtosis.

According to an embodiment, the method comprises:

determining an ion mobility value, collision cross section or interaction cross section difference between an ion mobility value, collision cross section or interaction cross section calculated under first analytical conditions and an ion mobility value, collision cross section or interaction cross section calculated under second different analytical conditions;

setting one or more operational parameters of the mass spectrometer based on the determined ion mobility value, collision cross section or interaction cross section difference so as to maximise or enhance the subsequent ion mobility separation of the plurality of different analyte ions.

According to an embodiment, the one or more analytical conditions comprise one or more pre-ionisation, ionisation or post-ionisation conditions for generating the plurality of different analyte ions and/or one or more experimental or measurement conditions for measuring the plurality of different analyte ions.

According to an embodiment, the one or more analytical conditions are selected from the group consisting of:

(i) the composition and/or concentration of a salt, dopant, derivatisation agent, reagent, shift reagent, supercharging reagent or charge reduction reagent which is added to a liquid sample prior to ionisation;

(ii) the composition and/or concentration of a neutral gas, dopant gas, derivatisation agent gas, reagent gas, shift reagent gas, supercharging reagent gas or charge reduction reagent gas which is added to a gaseous or vapour phase sample prior to ionisation;

(iii) the composition and/or concentration of a neutral gas, reactive gas, dopant gas, derivatisation agent, reagent gas, shift reagent gas, supercharging reagent gas or charge reduction reagent gas which is arranged to interact or react with analyte ions after ionisation and/or prior to, the separation of the ions according to their ion mobility; and (iv) the composition and/or concentration of dopant ions, derivatisation ions, reagent ions, supercharging reagent ions or charge reduction reagent ions which are arranged to interact or react with analyte ions after ionisation and/or prior to the separation of the ions according to their ion mobility.

According to an embodiment, the one or more analytical conditions are selected from the group consisting of; (i) a condition and/or parameter that affects a charge state of the analyte ions; (ii) a condition and/or parameter that affects an energy level of the analyte ions; (iii) a condition and/or parameter that affects the kinetic energy of the analyte ions; (iv) a condition and/or parameter that affects an activation energy of the analyte ions; and (v) a condition and/or parameter that affects the conformational form or nature of the analyte ions.

According to an embodiment, the one or more analytical conditions are selected from the group consisting of: (i) an ionisation condition of an ion source; (ii) the type of ion source used to ionise a sample; (iii) a voltage setting of an ion source; (iv) an ionisation polarity of ions being generated by an ion source; (v) a flow rate of sample supplied to an ion source; (vi) one or more liquid chromatography conditions of a liquid chromatography system; (vii) a composition of a liquid chromatography solution or solvent; and (viii) a liquid chromatography flow rate.

According to an embodiment, the one or more analytical conditions are selected from the group consisting of: (i) subjecting ions to hydrogen deuterium exchange; (ii) one or more hydrogen deuterium exchange conditions; (iii) subjecting ions to activation, photo-activation, dissociation or photo-dissociation; (iv) one or more dissociation, photo-dissociation, activation, and/or photo-activation conditions; (v) subjecting ions to heating or RF heating; (vi) one or more heating or RF heating conditions; (vii) subjecting ions to electromagnetic radiation, microwave radiation or laser irradiation (viii) one or more electromagnetic radiation, microwave radiation or laser irradiation conditions; (ix) subjecting ions to fragmentation or reaction; and (x) one or more fragmentation or reaction conditions.

According to an embodiment, the one or more analytical conditions are selected from the group consisting: (i) a voltage applied to an ion-optical component; (ii) a route taken by analyte ions through a portion of the mass spectrometer; (iii) the transit time of analyte ions through a portion of the mass spectrometer; (iv) one or more pressures within the mass spectrometer; (v) one or more temperatures within the mass spectrometer; (vi) the composition of a gas within the mass spectrometer; and (vii) the strength of an electric filed within the mass spectrometer.

According to an embodiment, the one or more analytical conditions are selected from the group consisting of: (i) the composition of an ion mobility separation or buffer gas; (ii) the composition of one or more additives, one or more dopants and/or one or more reagents added to an ion mobility separation or buffer gas; (iii) the flow rate and/or direction of an ion mobility separation or buffer gas; (iv) the pressure or number density of an ion mobility separation or buffer gas; (v) the temperature within an ion mobility separation device; (vi) the strength of an electric field within an ion mobility separation device; (vii) the path length traveled by ions within an ion mobility separation device; (viii) the residence time of ions within an ion mobility separation device; (ix) the initial width of an ion pulse introduced into an ion mobility separation device; and (x) the speed, amplitude or repeat pattern of a travelling DC wave within an ion mobility separation device.

According to an embodiment, the step of calculating the ion mobility value, collision cross section or interaction cross section comprises:

calculating a three dimensional structure of one or more of the plurality of different analyte ions; and calculating one or more of the ion mobility value, collision cross section or interaction cross section using the three dimensional structure.

According to an embodiment, the step of calculating the ion mobility value, collision cross section or interaction cross section comprises calculating the effects of electronic interactions of the plurality of different analyte ions with a polar or polarisable ion mobility separation or buffer gas.

According to an aspect there is provided a mass spectrometer comprising a control system arranged and adapted to:

calculate an ion mobility value, a collision cross section or interaction cross section of a plurality of different analyte ions under one or more different analytical conditions; and set one or more operational parameters of the mass spectrometer in response to the calculated ion mobility values, collision cross sections or interaction cross sections so as to maximise or enhance a subsequent ion mobility separation of a plurality of different analyte ions.

According to an embodiment, given two or more known target analytes or isomers, the structures and theoretical collision cross section ("CCS") values for a range of different gas phase ions derived from these analytes are may systematically calculated under different solution phase and/ or gas phase conditions and/or under different ion mobility spectrometry or separation conditions. Based on these calculations the optimum analytical conditions under which these analytes will efficiently separate by ion mobility spectrometry or separation are then may predicted. This prediction is then may used to set a subsequent ion mobility spectrometry or separation experiment so that the experiment is optimized for each target compound. The list of various ionic forms of the target compounds and ion mobility spectrometry or separation conditions may be limited to those available within a specific laboratory or for a specific ion source or ion mobility spectrometry or separation design.

According to an aspect there is provided a method of ion mobility spectrometry comprising:

(a) identifying two or more compounds or isomeric forms of a compound or compounds which are to be separated by ion mobility;

(b) calculating theoretical structures for a variety of gas phase ions of these compounds or derived from these compounds which may be formed by altering solution phase or gas phase chemistry;

(c) calculating theoretical collision cross section or interaction cross section values for each of these said ions under a variety of different ion mobility spectrometry or separation conditions;

(d) from the theoretically calculated CCS values determining the experimental gas phase or solution phase conditions of the instrument, which are most likely to give optimal ion mobility spectrometry or separation of these species; and then (e) analysing these species by ion mobility spectrometry or separation using the optimal conditions.

The variety of gas phase ions may include different charge carriers such as sodium, potassium, lithium, chlorine, bromine, fluorine, iodine etc. Different adduct or derivitisation agents, different charge states etc.

The different ion mobility spectrometry or separation conditions may include the use of different drift media such as polarisable or polar drift gasses and dopants or introduction of energy into the ions as they separate by ion mobility spectrometry or separation to alter the gas phase structure.

The ion mobility spectrometry or separation may be coupled with mass spectrometry.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer may further comprise a device arranged and adapted to supply an AC or RF voltage to the electrodes. The AC or RF voltage may have an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage may have a frequency selected from the group consisting of: (i)<100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The mass spectrometer may comprise a chromatography detector.

The chromatography detector may comprise a destructive chromatography detector may selected from the group consisting of: (i) a Flame Ionization Detector ("FID"); (ii) an aerosol-based detector or Nano Quantity Analyte Detector ("NQAD"); (iii) a Flame Photometric Detector ("FPD"); (iv) an Atomic-Emission Detector ("AED"); (v) a Nitrogen Phosphorus Detector ("NPD"); and (vi) an Evaporative Light Scattering Detector ("ELSD").

Additionally or alternatively, the chromatography detector may comprise a non-destructive chromatography detector may selected from the group consisting of: (i) a fixed or variable wavelength UV detector; (ii) a Thermal Conductivity Detector ("TCD"); (iii) a fluorescence detector; (iv) an Electron Capture Detector ("ECD"); (v) a conductivity monitor; (vi) a Photoionization Detector ("PID"); (vii) a Refractive Index Detector ("RID"); (viii) a radio flow detector; and (ix) a chiral detector.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation may comprise interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which:

FIG. 1 shows a flow diagram according to an embodiment.

DETAILED DESCRIPTION

An embodiment is directed to a method in which a collision cross section or interaction cross section of a plurality of different analyte ions under one or more different analytical conditions, may under one, two or more different pre-ionisation, ionisation and/or post-ionisation conditions for generating the plurality of different analyte ions and/or one or more experimental or measurement conditions for measuring the plurality of different analyte ions, may be theoretically calculated, and then one or more of the one or more different analytical conditions may be selected based on the calculated collision cross sections or interaction cross sections so as to maximise or enhance a subsequent ion mobility separation of the plurality of different analyte ions using a mass spectrometer. One or more operational parameters of the mass spectrometer may be set based on the calculated collision cross sections or interaction cross sections, so as to produce the one or more selected analytical conditions so as to maximise or enhance the subsequent ion mobility separation of the plurality of different analyte ions using the mass spectrometer.

The embodiment may involve determining or predicting a plurality of different analyte ions which may be generated from one or more analytes of interest under one or more of the different analytical conditions, e.g. under one, two or more different pre-ionisation, ionisation and/or post-ionisation conditions, calculating the collision cross section or interaction cross section for each of the determined or predicted different analyte ions, and then selecting one or more of the different analytical conditions.

Additionally or alternatively, the embodiment may involve calculating a collision cross section or interaction cross section for a plurality of different analyte ions under one, two or more different experimental or measurement conditions, and then selecting one or more of the one or more different experimental or measurement conditions so as to maximise or enhance the subsequent ion mobility separation of the plurality of different analyte ions.

According to an embodiment, one or more additional physico-chemical or other properties of the plurality of different analyte ions, such as ion mobility peak shape, Ion mobility peak width, ion mobility peak skew, number of ion mobility peaks and/or ion mobility peak kurtosis, may also be calculated under the one or more different analytical conditions, and may be used to set the one or more operational parameters of the mass spectrometer so as to maximise or enhance the subsequent ion mobility separation of the plurality of different analyte ions. For example, it may be the case that different ions, e.g. protomer ions, can be separated, e.g. into two or more peaks, under certain conditions, such as in $CO_2$, and not under other conditions, such as in He or $N_2$.

According to an embodiment, a collision cross section or interaction cross section difference between a collision cross section or interaction cross section calculated under first analytical conditions and a collision cross section or interaction cross section calculated under second different analytical conditions may be determined and used to select the analytical conditions and may be used to set the one or more operational parameters of the mass spectrometer.

According to various embodiments, the separation of species or isomers may be improved, or altered, by choice of charge state, charge carrier or derivatisation agent. Additionally or alternatively, the choice of ion mobility spectrometry or separation drift media can be used to affect the separation by ion mobility spectrometry or separation. In one embodiment, polarisable drift gas or drift media e.g. containing gas phase neutrals with a permanent dipole moment may be used to selectively change the separation of different analytes or isomers of an analyte. The interaction of polarisable or polar neutrals with ions depends on the electronic structure of the ions (local or bulk dipole moments) which may be very specific to a given structure.

According to an embodiment, given a known compound identity, three dimensional gas phase structures may be calculated for ions formed from this compound. Molecular mechanics and quantum chemistry modelling approaches may be employed to do this, Commercially available software such as Gaussian (www.gaussian.com) may be used to perform such calculations.

From these structures theoretical collision cross sections may be calculated using software such as MobCal from Indiana University. Reference is made to: A. A. Shvartsburg and M. F. Jerrold, "An Exact Hard Spheres Scattering Model for the Mobilities of Polyatomic Ions", Chem. Phys. Lett. 1996, 261, 86-91.

The effect on apparent collision cross section ("CCS") of long range electronic interactions between ions and polar or polarisable molecules in the ion mobility spectrometry or separation drift media (buffer gas) may be taken into account within these calculations, e.g. in effect to calculate an interaction cross section.

FIG. 1 shows a flow diagram illustrating an embodiment.

In step 1 target analytes are may identified. For example, for a particular analysis it may be known that two compounds with identical or very similar mass to charge ratio ions may be present. These may be stereo or positional isomers or the compounds may have entirely different elemental composition or structure. Additionally or alternatively, they may be conformers of the same compound. Mass spectrometry alone may be unable to separate these species either because they have the same mass to charge ratio or because the mass resolution of the analyser used is insufficient.

Additionally or alternatively, a group of known target compounds may may be chosen for a particular analysis. For example, targeted pesticides, peptides, lipids or carbohydrates may be chosen.

In each case it is the purpose of an embodiment to determine the experimental conditions such that the ion mobility spectrometry or separation of two or more of these target compounds or two or more ions of a compound may be optimized.

According to the preferred embodiment, optimization of ion mobility spectrometry or separation can improve subsequent identification and quantification of isobaric or nominally isobaric compounds and reduce interferences in the ion mobility spectrometry or separation spectra allowing more accurate calculation of cross section and peak areas.

In step 2 a range of possible analysis conditions are may chosen.

Depending on the facilities within a particular laboratory and the flexibility of the design of the ion mobility device, the ion source and/or inlet to the ion source, a range of different conditions may be investigated and used. The following list of preferred conditions is not exhaustive.

Different Solution and Gas Phase Chemistry May be Utilised in Order to Alter the Nature of the Gas Phase Ions Generated from the Analytes In embodiments that use Electrospray ionisation, addition of a salt solution into the analyte flow prior ionization can allow the charge carrier which will appear on the analyte ion to be controlled and/or produce known adducts. For example, in embodiments that use positive ion Electrospray, addition of formic acid results in predominantly protonated ions $[M+nH]^{n+}$ being formed wherein n is the number of charges. Addition of sodium chloride NaCl results in predominantly sodiated ions $[M+nNa]^{n+}$ being formed.

In general adducts of the form $[M+nY]^{n+}$ may be formed by addition of a suitable soluble ionic salt wherein Y=Na, K, Li, H, $NH_3$ etc.

In embodiments that use negative ion mode, adducts may be formed in a similar manner. For example, adducts may be formed by addition of soluble salts to give $[M+X]^-$ wherein X=F, Cl, Br, I, $NO_3$ etc. In negative ion $[M-nH]^{-n}$ may be produced by addition of ammonium hydroxide for example.

Many more embodiments of differing solution phase chemistry are contemplated. In some embodiments more complex or larger derivatising agents may be investigated and used may based on knowledge of the chemical reactivity of the analytes.

For example, in embodiments that use gas chromatography ("GC") MS acylation, silylation, alkylation and/or esterification may be used, these being common derivatisation methods using commercially available derivatisation reagents. In embodiments that use liquid chromatography ("LC") MS, Schiffbase forming reagents, primary and secondary amines and/or chromopores for fluorometric detection may be used, these being commonly available reagents. In these embodiments, derivatisation may be performed offline prior to separation.

In some embodiments, derivatisation of the ionized analyte may be performed in the gas phase either prior to ion mobility spectrometry or separation and/or within the ion mobility spectrometry or separation device. This may be achieved, for example, by the addition of reactive neutral and/or charged species into an RF confined reaction cell e.g. at sub atmospheric pressure.

In an embodiment, supercharging and/or charge reduction may additionally or alternatively be used to predictably alter the nature of the ions formed from the analyte.

According to an embodiment, the charge state of an ion may be manipulated either in the solution phase prior to ionization and/or in the gas phase, e.g. by so called supercharging and/or charge reduction techniques. For example, in embodiments that use Electrospray Ionisation ("ESI"), addition of mNBA ("m-nitrobenzyl alcohol"), tetramethylene sulfone ("sulfolane") and/or dimethyl sulfoxide ("DMSO") can result in an increase in the intensity of higher charged ions.

In an embodiment, charge reduction of analyte ions may be performed, e.g. by using an atmospheric or sub-atmospheric neutralization chamber employing corona discharge and/or ultraviolet ("UV") radiation and/or another energy source to produce reagent ions which may be caused to interact with the analyte ions resulting in a lowering of the analyte ions' charge state. In other embodiments, basic compounds such as triethylammonium bicarbonate and/or imidazole may be added in solution prior to ionization and/or basic molecules may be introduced in the gas phase e.g. at atmospheric or sub-atmospheric pressure so as to interact with the analyte ions.

In embodiments that use different ionization techniques, such as Atmospheric Pressure Chemical Ionisation ("APCI") or sub atmospheric pressure chemical ionization, Matrix Assisted Laser Desorption Ionisation ("MALDI"), etc., other reagents and/or methods of manipulating the chemical nature of the analyte ions may be used.

In all of these embodiments, the nature of the ions produced from the analyte is predictable. In an embodiment, a single analyte may be manipulated to produce several different types of gas phase ions, depending on the solution phase and/or gas phase chemistry available.

According to an embodiment a number of different alternative experiments may be contemplated that give rise to a number of different forms of the same analyte ion. The expected or predicted analyte ion species may then be theoretically modelled, and the theoretical ion mobility spectrometry or separation behaviour may be examined in order to determine which will yield the optimum results before any experimentation.

Different IMS Drift Gas Compositions

The choice of ion mobility spectrometry or separation drift media can dramatically affect separation by ion mobility spectrometry or separation. According to an embodiment, a polarisable drift gas, buffer gas or drift media containing gas phase neutrals e.g. with a permanent dipole moment may be used to selectively change the separation of different analyte ions or isomer ions of an analyte. According to an embodiment, a selection of different drift gas compositions may be made and the predicted effect on the analyte ions mobility may be investigated by theoretical Collision Cross Section CCS calculation. Depending on the electronic structure of the analyte ions, ion mobility spectrometry or separation may be superior in one drift gas compared to another drift gas.

Different Pre-IMS or Intra-IMS Activation Energy

According to an embodiment, activation of an ion e.g. to raise internal temperature by an arbitrary or known amount may be used to cause unfolding and/or transition between conformational states. In various embodiments, lasers and/or other energy sources may be used to excite ions may before and/or during ion mobility spectrometry or separation.

Returning now to FIG. 1, in step 3 theoretical Collision Cross Section CCS values may be calculated for the analyte ions under the different experimental conditions or combinations of the different experimental conditions proposed in step 2.

In step 4 a theoretical ion mobility or two dimensional ion mobility-mass to charge ratio drift time spectrum may be produced based on the calculated Collision Cross Section CCS, mass to charge ratio and charge state of the analyte and optionally the known operational parameters of the ion mobility spectrometry or separation system to be used for each of the proposed experimental conditions for which theoretical Collision Cross Section CCS values have been calculated.

The operational parameters of the ion mobility spectrometry or separation device may include pressure or number density of the ion mobility spectrometry or separation drift gas, temperature, electrostatic field, ion mobility spectrometry or separation cell path length, and/or the initial width of the ion pulse introduced into the ion mobility spectrometry or separation device, etc. For embodiments that use traveling wave ion mobility spectrometry or separation, the wave amplitude velocity and repeat pattern may also be considered and used.

According to an embodiment, the operational parameters may include the path length traveled by ions within an ion mobility separation device and/or the residence time of ions within an ion mobility separation device. The path length traveled by ions within an ion mobility separation device and/or the residence time of ions within an ion mobility separation device may be set to the minimum such that the different ions are still sufficiently resolved. This advantageously minimises the time and/or path length required for a given experiment.

In step 5 the conditions for optimum separation of the analyte ions, e.g. based on examination of the theoretical ion mobility spectrometry or separation data calculated in step 4, may be determined.

Finally, in step 6 the analysis may be performed using the analyte under the optimum experimental conditions determined during the previous steps to produce experimental data.

According to an embodiment, the approach of the above described embodiment may be used to predict the best conditions for tandem IMS-IMS experiments. In this embodiment, the Collision Cross Section CCS and therefore ion mobility spectrometry or separation drift time for the analyte ions traversing two sequential ion mobility spectrometry or separation devices optionally with different separation conditions may be calculated. This information may be used to design the optimum combination of IMS-IMS separation conditions for an analyte mixture.

According to an embodiment, optimum conditions for product ions and/or precursor ions may be theoretically determined, considered and used.

The method or workflow according to an embodiment can be applied to differential ion mobility or Field Asymmetric ion Mobility Spectrometry FAIMS, optionally using a suitable mathematical model relating ion mobility spectrometry or separation to gas phase structure and drift media.

It will be appreciated that in an embodiment the ion mobility spectrometry or separation experimental conditions may be directed by theoretical calculation of the mobility of the analyte ions e.g. under different solution and gas phase conditions to allow an optimized ion mobility spectrometry or separation experiment to be designed based on the theoretical calculations. This reduces the experimental time required to find the optimum conditions for different target analytes and conserves samples which may be difficult to obtain in sufficient quantity for extensive experimental optimization.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
calculating an ion mobility value, collision cross section or interaction cross section of a plurality of different analyte ions under one or more different analytical conditions; and
setting one or more operational parameters of a mass spectrometer in response to said calculated ion mobility values, collision cross sections or interaction cross sections so as to maximise or enhance a subsequent ion mobility separation of a plurality of different analyte ions;
wherein said step of setting said one or more operational parameters of said mass spectrometer comprises selecting one or more of said one or more different analytical conditions based on said calculated ion mobility values, collision cross sections or interaction cross sections so as to maximise or enhance said subsequent ion mobility separation of said plurality of different analyte ions, and setting said one or more operational parameters of said mass spectrometer so as to produce said one or more selected analytical conditions; and wherein said one or more analytical conditions comprise one or more pre-ionisation, ionisation or post-ionisation conditions for generating said plurality of different analyte ions.

2. A method as claimed in claim 1, wherein:
said plurality of different analyte ions relate to the same analyte but have different forms, structures, states or other properties; or
said plurality of different analyte ions relate to different analytes having different compositions, forms, structures, states or other properties.

3. A method as claimed in claim 1, further comprising:
determining, calculating or predicting a plurality of different analyte ions which may be generated from one or more analytes of interest under one or more of said different analytical conditions;
wherein said step of calculating said ion mobility value, collision cross section or interaction cross section of said plurality of different analyte ions under said one or more different analytical conditions comprises calculating an ion mobility value, collision cross section or interaction cross section for one or more of said determined, calculated or predicted different analyte ions.

4. A method as claimed in claim 1, further comprising separating said plurality of different analyte ions according to their ion mobility or according to their rate of change of ion mobility with electric field strength one or more times using said mass spectrometer.

5. A method as claimed in claim 1, further comprising generating said plurality of different analyte ions using said mass spectrometer.

6. A method as claimed in claim 1, further comprising mass analysing said plurality of different analyte ions using said mass spectrometer.

7. A method as claimed in claim 1, further comprising:
calculating one or more additional physico-chemical or other properties of said plurality of different analyte ions under said one or more different analytical conditions; and
setting one or more operational parameters of said mass spectrometer based on said calculated additional physico-chemical or other properties so as to maximise or enhance said subsequent ion mobility separation of said plurality of different analyte ions.

8. A method as claimed in claim 7, wherein said one or more additional physico-chemical or other properties comprise peak shape, peak width, peak skew, number of peaks and/or peak kurtosis.

9. A method as claimed in claim 1, wherein said method comprises:
determining an ion mobility value, collision cross section or interaction cross section difference between an ion mobility value, collision cross section or interaction cross section calculated under first analytical conditions and an ion mobility value, collision cross section or interaction cross section calculated under second different analytical conditions; and
setting one or more operational parameters of said mass spectrometer based on said determined ion mobility value, collision cross section or interaction cross section difference so as to maximise or enhance said subsequent ion mobility separation of said plurality of different analyte ions.

10. A method as claimed in claim 1, wherein said one or more analytical conditions further comprise one or more experimental or measurement conditions for measuring said plurality of different analyte ions.

11. A method as claimed in claim 1, wherein said one or more analytical conditions are selected from the group consisting of:
(i) the composition and/or concentration of a salt, dopant, derivatisation agent, reagent, shift reagent, supercharging reagent or charge reduction reagent which is added to a liquid sample prior to ionisation;
(ii) the composition and/or concentration of a neutral gas, dopant gas, derivatisation agent gas, reagent gas, shift reagent gas, supercharging reagent gas or charge reduction reagent gas which is added to a gaseous or vapour phase sample prior to ionisation;
(iii) the composition and/or concentration of a neutral gas, reactive gas, dopant gas, derivatisation agent, reagent gas, shift reagent gas, supercharging reagent gas or charge reduction reagent gas which is arranged to interact or react with analyte ions after ionisation and/or prior to the separation of said ions according to their ion mobility; and
(iv) the composition and/or concentration of dopant ions, derivatisation ions, reagent ions, supercharging reagent ions or charge reduction reagent ions which are arranged to interact or react with analyte ions after ionisation and/or prior to the separation of said ions according to their ion mobility.

12. A method as claimed in claim 1, wherein said one or more analytical conditions are selected from the group consisting of: (i) a condition and/or parameter that affects a charge state of said analyte ions; (ii) a condition and/or parameter that affects an energy level of said analyte ions; (iii) a condition and/or parameter that affects the kinetic energy of said analyte ions; (iv) a condition and/or parameter that affects an activation energy of said analyte ions; and (v) a condition and/or parameter that affects the conformational form or nature of said analyte ions.

13. A method as claimed in claim 1, wherein said one or more analytical conditions are selected from the group consisting of: (i) an ionisation condition of an ion source; (ii) the type of ion source used to ionise a sample; (iii) a voltage setting of an ion source; (iv) an ionisation polarity of ions being generated by an ion source; (v) a flow rate of sample supplied to an ion source; (vi) one or more liquid chromatography conditions of a liquid chromatography system; (vii) a composition of a liquid chromatography solution or solvent; and (viii) a liquid chromatography flow rate.

14. A method as claimed in claim 1, wherein said one or more analytical conditions are selected from the group consisting of: (i) subjecting ions to hydrogen deuterium exchange; (ii) one or more hydrogen deuterium exchange conditions; (iii) subjecting ions to activation, photo-activation, dissociation or photo-dissociation; (iv) one or more dissociation, photo-dissociation, activation, and/or photo-activation conditions; (v) subjecting ions to heating or RF heating; (vi) one or more heating or RF heating conditions; (vii) subjecting ions to electromagnetic radiation, microwave radiation or laser irradiation; (viii) one or more electromagnetic radiation, microwave radiation or laser irradiation conditions; (ix) subjecting ions to fragmentation or reaction; and (x) one or more fragmentation or reaction conditions.

15. A method as claimed in claim 1, wherein said one or more analytical conditions are selected from the group consisting: (i) a voltage applied to an ion-optical component; (ii) a route taken by analyte ions through a portion of said mass spectrometer; (iii) the transit time of analyte ions through a portion of said mass spectrometer; (iv) one or more pressures within said mass spectrometer; (v) one or more temperatures within said mass spectrometer; (vi) the composition of a gas within said mass spectrometer; and (vii) the strength of an electric filed within said mass spectrometer.

16. A method as claimed in claim 10, wherein said one or more experimental or measurement conditions are selected from the group consisting of: (i) the composition of an ion mobility separation or buffer gas; (ii) the composition of one or more additives, one or more dopants and/or one or more reagents added to an ion mobility separation or buffer gas; (iii) the flow rate and/or direction of an ion mobility separation or buffer gas; (iv) the pressure or number density of an ion mobility separation or buffer gas; (v) the temperature within an ion mobility separation device; (vi) the strength of an electric field within an ion mobility separation device; (vii) the path length travelled by ions within an ion mobility separation device; (viii) the residence time of ions within an ion mobility separation device; (ix) the initial width of an ion pulse introduced into an ion mobility separation device; and (x) the speed, amplitude or repeat pattern of a travelling DC wave within an ion mobility separation device.

17. A method as claimed in claim 1, wherein said step of calculating said ion mobility value, collision cross section or interaction cross section comprises:
calculating a three dimensional structure of one or more of said plurality of different analyte ions; and
calculating one or more of said ion mobility value, collision cross section or interaction cross section using said three dimensional structure.

18. A method as claimed in claim 1, wherein said step of calculating said ion mobility value, collision cross section or interaction cross section comprises calculating the effects of electronic interactions of said plurality of different analyte ions with a polar or polarisable ion mobility separation or buffer gas.

19. A mass spectrometer comprising a control system arranged and adapted:
(i) to calculate an ion mobility value, a collision cross section or interaction cross section of a plurality of different analyte ions under one or more different analytical conditions; and
(ii) to set one or more operational parameters of said mass spectrometer in response to said calculated ion mobility values, collision cross sections or interaction cross sections so as to maximise or enhance a subsequent ion mobility separation of a plurality of different analyte ions;
wherein said control system is arranged and adapted to set said one or more operational parameters of said mass spectrometer by selecting one or more of said one or more different analytical conditions based on said calculated ion mobility values, collision cross sections or interaction cross sections so as to maximise or enhance said subsequent ion mobility separation of said plurality of different analyte ions, and setting said one or more operational parameters of said mass spectrometer so as to produce said one or more selected analytical conditions; and
wherein said one or more analytical conditions comprise one or more pre-ionisation, ionisation or post-ionisation conditions for generating said plurality of different analyte ions.

* * * * *